United States Patent [19]

Berger

[11] Patent Number: 4,845,985
[45] Date of Patent: Jul. 11, 1989

[54] SUPERCRITICAL FLUID CHROMATOGRAPHY

[75] Inventor: Terry A. Berger, Landenberg, Pa.

[73] Assignee: Hewlett-Packard Company, Palo Alto, Calif.

[21] Appl. No.: 157,344

[22] Filed: Feb. 17, 1988

[51] Int. Cl.$^4$ ............................................. G01N 30/32
[52] U.S. Cl. ..................................... 73/23; 73/61.1 C
[58] Field of Search ........................... 73/23.1, 61.1 C; 210/198.2

[56] References Cited

U.S. PATENT DOCUMENTS

| 4,151,741 | 5/1979 | Schirrmeister | 73/23.1 |
| 4,271,695 | 6/1981 | Sisti et al. | 73/23.1 |
| 4,479,380 | 10/1984 | Novotny et al. | 73/61.1 C |

FOREIGN PATENT DOCUMENTS 0008747 1/1985 Japan ................................. 73/23.1

OTHER PUBLICATIONS

Chester, T. L.-Journal of Chromatography, 299-pp. 424-431, (1984)-Printed in The Netherlands.
Crowther, Jonathan B., et al.-Analytical Chemistry, vol. 57, No. 13-pp. 2711-2716-Nov. 1985-USA.
Gere, Dennis R.-Science, vol. 222-pp. 253-259-Oct. 21, 1983-USA.
Guthrie, E. J., et al.,-Journal of Chromatographic Science, vol. 24-pp. 236-241-Jun., 1986-USA.
Schwartz, Herbert E., et al.,-LC-GC, vol. 5, No. 6-pp. 490-497-USA.
Smith, Richard D., et al.-Analytical Chemistry, vol. 58, No. 9, pp. 2057-2064-Aug., 1986-USA.
White, C. M., et al.-Journal of High Resolution Chromatography & Chromatography Communications, vol. 9-pp. 4-17, Jan., 1986-USA.

Primary Examiner—Stewart J. Levy
Assistant Examiner—Joseph W. Roskos
Attorney, Agent, or Firm—Richard F. Schuette

[57] ABSTRACT

In a system for analyzing a chemical sample by chromatographic separation of said sample into components a method and apparatus are provided for maximizing detector resolution and minimizing duration by maintaining the linear velocity of the mobile phase at a desired level by affecting the viscosity and density characteristics of the mobile phase as it passes through a restrictor by programming the restrictor temperature.

12 Claims, 4 Drawing Sheets

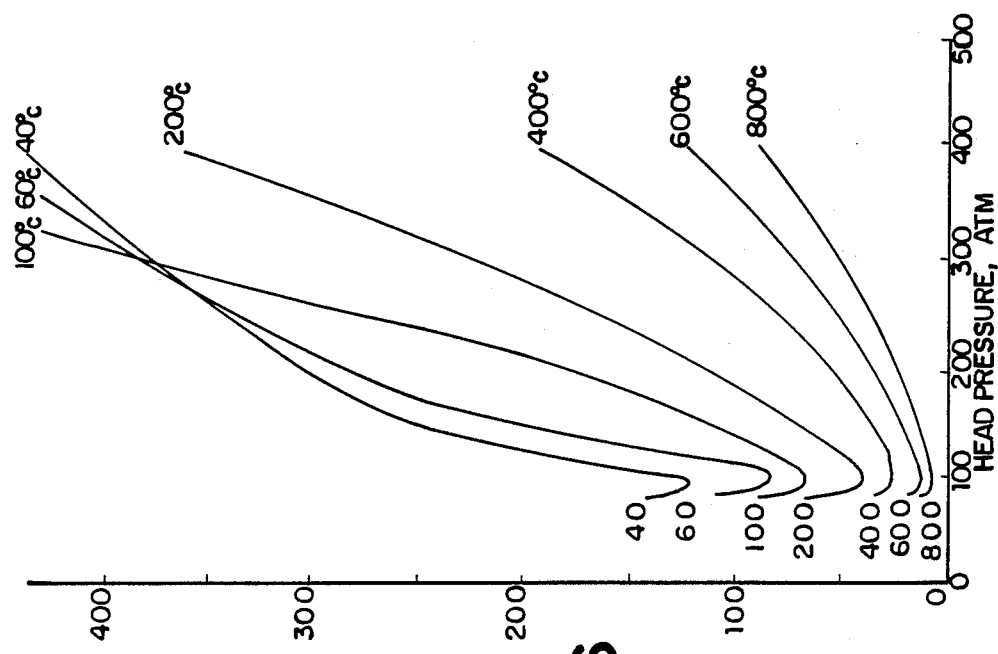
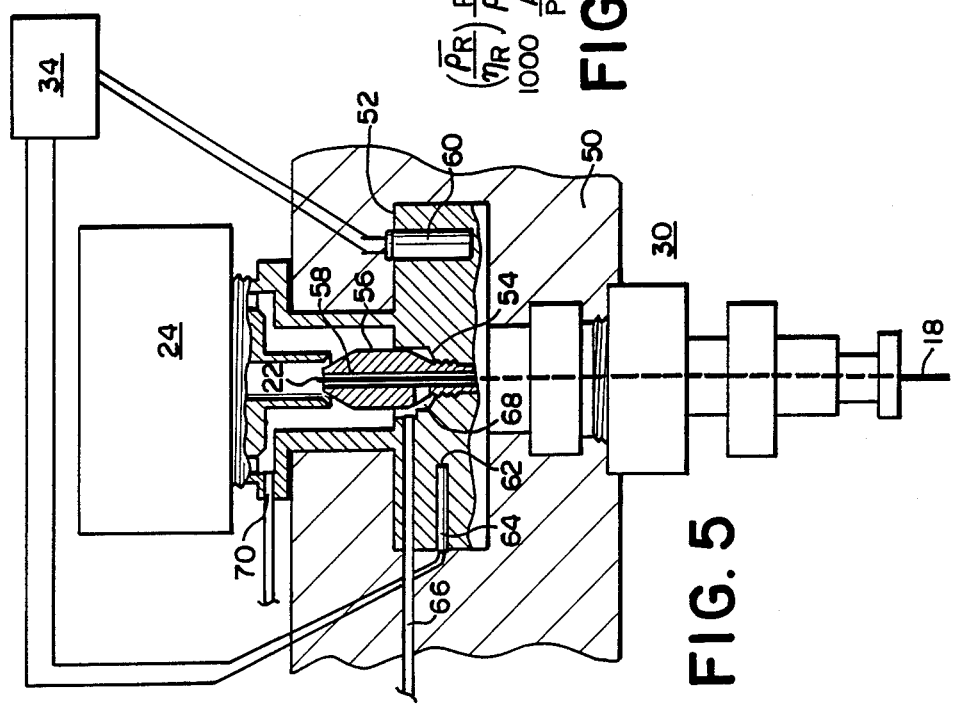
FIG. 6
FIG. 5

SUPERCRITICAL FLUID CHROMATOGRAPHY

FIELD OF THE INVENTION

The present invention relates to an advancement in the art of Supercritical Fluid Chromatography (SFC) and, more particularly, to an SFC system having improved resolution capabilities and minimized test durations.

BACKGROUND OF THE INVENTION

In analytical chemistry, liquid and gas chromatography techniques have become important tools in the identification of chemical sample components. The basic principle underlying all chromatographic techniques is the separation of a sample chemical mixture into individual components by transporting the mixture in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

Consider, for example, a gas chromatograph. Typically, a supply of inert carrier gas (mobile phase) is continually passed as a stream through a heated column containing porous sorptive media (stationary phase). A sample of the subject mixture is injected into the mobile phase stream and passed through the column. A detector, positioned at the outlet end of the column, detects each of the separated components as they exit the column. Separation is due primarily to differences in the volatility characteristics of each sample component at the temperature in the column.

The analytical choice between liquid and gas chromatography techniques is largely dependent on the molecular weight of the compound being analyzed. Liquid chromatographs are capable of analyzing much heavier compounds than gas chromatographs. However, since gas chromatography detection techniques are more sensitive, they are preferred.

The advent of Supercritical Fluid Chromatography (SFC) provided a potential bridge between gas and liquid chromatography advantages, i.e., high sensitivity and heavier molecular weight samples. In SFC, a fluid heated above the critical point, is used as the mobile phase. Such fluid is passed under pressure through a media which differentially retains sample components. As the pressure of the mobile phase is increased, for example, from about 40 ATM to approximately 400 ATM, the sample being analyzed separates into its various components dependent upon the relative differential solubility of each component with the mobile phase. Since the mobile phase is a gas, gas chromatography detectors can be utilized, significantly enhancing detection sensitivity and selectivity. SFC can be simplistically viewed as an extension of gas chromatography to higher molecular weight components. SFC has been found to be primarily useful in the analysis of moderate molecular weight homologous series (M.W. 100 to 10,000) and some thermally labile molecules such as pesticides and pharmaceuticals.

Due to problems with analysis times and resolution, SFC as an analytical tool has not achieved its full potential. The term "resolution" as used herein refers to the distinctiveness with which component peaks appear in an SAFC chromatogram. Chromatograms are those graphs of detector output signal vs. time which are produced by the connection of an X-Y plotter or other chart recorder to a chromatograph detector, wherein a peak indicates the detection of a component.

Originally, SFC systems used media packed columns similar to those used in liquid chromatography. However, due to concerns over large pressure drops, decreased efficiency and poor media stability, the use of capillaries in place of media packed columns as the stationary phase has become generally accepted. SFT systems utilizing a stationary phase coated capillaries are generally referred to as capillary SFC systems. Systems of this type will find the present invention of primary usefulness.

Consider generally the block diagram of the capillary SFC system shown in FIG. 1. A mobile phase fluid is supplied to a pump which in turn supplies the fluid to an injector. The sample to be analyzed is injected into the mobile phase and the combination is supplied to a splitter. Since capillary SFC utilizes a very small sample volume, typically on the order of 10 Nanoliters, a splitter is incorporated to ensure that only the allowed volume of the combination is passed through the capillary for analysis. Since SFC is carried out under predetermined pressure conditions, either static or programmed dynamic pressure conditions, a restrictor is placed at the capillary outlet and at the non-analyzed splitter output to limit mass flow. Pressure in this system is controlled by the pump. The capillary restrictor output is passed through a detector, which as mentioned previously, is preferably a gas chromatography type detector, such as a Flame Ionization Detector (FID). The output of the detector, a voltage signal, is applied to an X-Y plotter or some form of chart recorder which graphs detector output vs. time. Since pressure is also changed over time, for example, increasing the pump pressure at a fixed rate, the SFC chromatogram is also a reflection of detector output vs. pressure.

As will be understood, the splitter design and the restrictors function to create a flow ratio such that the nanoliter capillary volume is maintained. This ratio is also referred to as the split ratio.

As mentioned previously, SFC has not reached its maximum potential because it exhibits substantially lower speed and less resolution than gas chromatography. It can be shown that at the same theoretical efficiency, (i.e. numbers of theoretical plates), on the same diameter column, SFC systems are approximately 1000 times slower than gas chromatographs. By using even a smaller internal diameter capillary, SFC can be shown to be approximately 200 times slower than gas chromatography on larger capillary columns. Attempts to resolve the time problem with SFC systems typically have involved operation of smaller diameter columns at many times optimum linear velocity and modifying pressure programming, i.e., increasing the pressure at different rates during the test cycle. Unfortunately, these approaches significantly reduce resolution in known SFC systems. FIG. 2 is an example of such resolution reduction. The peaks which should be distinctly detected (dashed lines) in the latter stages of the analysis are lost in an aggregate signal.

The primary reason for such poor resolution is the effect which programmed pressure schemes and system design have on the linear velocity of the mobile phase solution. It was previously thought that capillary linear velocity remained constant during pressure programmed tests. However, it has been shown that this is not true. What may not be generally acknowledged is that as linear velocity increases, SFC efficiency decreases significantly. The most widely used capillary columns in SFC have an internal diameter of 50 um. Typical solute diffusion coefficients center around $1 \times 10^{-4}$ sq.cm/sec. Using the Golay equation, uncorrected for gas non-idealities, a simple graph of theoretical plates vs. column linear velocity can be generated as in FIG. 3, showing the significant decrease in column efficiency with increasing linear velocity.

More particularly, as pump pressure is increased, the pressure drop across the restrictor increases. Increasing the pressure drop across the restrictor causes mass flow to increase. If the density and viscosity of the mobile phase were constant at all pressures, mass flow would increase in direct proportion to pressure. However, density and viscosity and the ratio of the two are not constant with pressure but change greatly. The combination of pressure and the ratio of density to viscosity mean that mass flow can increase enormously over the pressure range typically encountered in a pressure programmed run.

Increasing pressure increases column density at the same time. This has the effect of decreasing column linear velocity at a fixed mass flow rate, mitigating some of the effects of greatly increased mass flow through the restrictor. However, programming from 80 to 400 ATM can increase mass flow rate more than 50 times and column linear velocity more than 10 times. Such increases will not only greatly reduce the time a component remains in the capillary [retention time] and chromatogram peak widths, but will also degrade resolution.

Consequently, there is a significant need in capillary SFC to control capillary linear velocity and pressure independently, particularly during pressure programmed operation. Present instrumentation controls pressure or density only. Independent adjustment of linear velocity would allow a constant column efficiency and resolution and could also allow adjustment of a speed/resolution trade-off in different parts of the chromatogram.

Since solute diffusion coefficients in SFC are on the order of $1 \times 10^{-4}$ sq.cm./sec, the optimum linear velocity of mobile phase through a capillary column can be shown to be in the range of 0.1 to 0.5 cm/sec. Higher linear velocity decreases chromatographic resolution, degrading performance. For modest resolution chromatography on a 10 meter $\times$ 50 um ID column, maximum linear velocity should be no more than 10 cm/sec. Between these limits the mass flow rate of the mobile phase is between 0.5 and $1000 \times 10^{-6}$ g/sec. As is known, such optimum linear velocities can be determined utilizing Van Deemter plots.

Since mobile phase density increases with pressure, mass flow must increase in order to maintain constant column (capillary) linear velocity since:

$$\bar{u} = \frac{F}{\rho A}$$

where $\bar{u}$ = average linear velocity in the column in cm/sec; F = mass flow rate in g/sec; $\rho$ = density of the mobile phase in the column in g/cubic cm; and A = column cross sectional area in sq. cm. An ideal mass flow controller in an SFC system similar to that shown in FIG. 1 would allow adjustment of mass flow to increase, maintain or even decrease linear velocity regardless of head (pump) pressure.

Existing adjustable mechanical flow controllers tend to have large dead volumes. Since capillary SFC columns can produce solute peak volumes (volume of mobile phase containing 99% of a solute at the column exit) of less than 100 nanoliters, any flow controller must have a dead volume less than 20 nanoliters to avoid degrading the separation. In addition, flow controllers for capillary SFC must typically be mounted inside the base of gas chromatographic detectors where temperatures can be quite high. Typical temperatures of 200° to 400° C. and even 800° C. are employed. A flow controller must be capable of operating over this temperature region. There are no viable adjustable flow controllers available with the desired characteristics.

In the absence of an adjustable flow controller, fixed geometry restrictors such as pinholes or 5–20 cm long-$\times$4–10 um, ID tubes are widely used. Capillary tubes drawn down to pinholes with short-to-long internal tapers are also widely used.

However, different restrictors have different mass flow characteristics dependent upon operating conditions. Consequently, if one wishes to operate under similar efficiencies for different operating conditions, restrictors should be changed. If restrictors are not changed as column pressure is increased during a test run, initially there will be a slight decrease followed by a rapid increase in linear velocity. Since it is not possible to change restrictors with different characteristics (e.g., different length and internal diameter), as pressure is increased, compromises have been made heretofore with regard to resolution and time.

SUMMARY OF THE INVENTION

Therefore it is an object of the present invention to provide a method and apparatus for analyzing a chemical sample by chromatographic separation which maintains substantially uniform efficiency.

It is a further object of the invention to provide a method and apparatus for analyzing a chemical sample by chromatographic separation which maximizes resolution and minimizes analysis duration.

It is a further object of the invention to provide a method and apparatus for controlling linear velocity of the mobile phase during a chromatographic analysis.

It is a further object of the invention to provide a method and apparatus for controlling the linear velocity of mobile phase during a chromatographic analysis by heating the mobile phase.

It is yet another object of the invention to provide a method and apparatus for controlling changes in the linear velocity of a mobile phase during a chromatographic analysis where pressure is changing by affecting the viscosity and density characteristics of the mobile phase.

These and other objects of the invention are achieved and previously described difficulties are overcome in a system for analyzing a sample by chromatographic separation, which system includes a novel method and apparatus for controlling the linear velocity of the mobile phase as it passes through a stationary phase member, which method and apparatus affect the viscosity and density characteristics of the mobile phase for a given mobile phase pressure by maintaining the mobile phase temperature at a desired level.

These and other objects and advantages of the invention will become more apparent from the following detailed description when taken in conjunction with the following drawings.

BRIEF DESCRIPTION OF THE DRAWINGS

FIG. 5 is a partial cutaway view of a portion of the restrictor/detector arrangement shown in FIG. 4;

FIG. 6 is a graph of a calculated linear velocity vs. pressure where the chromatograph column is heated to 40° C. and the restrictor is heated to various temperatures from 40° C. to 800° C.;

DETAILED DESCRIPTION OF THE PREFERRED EMBODIMENT

As will be described with regard to FIGS. 4-8, the present invention is embodied in a novel apparatus and method for Supercritical Fluid Chromatography (SFC).

Figure 4:
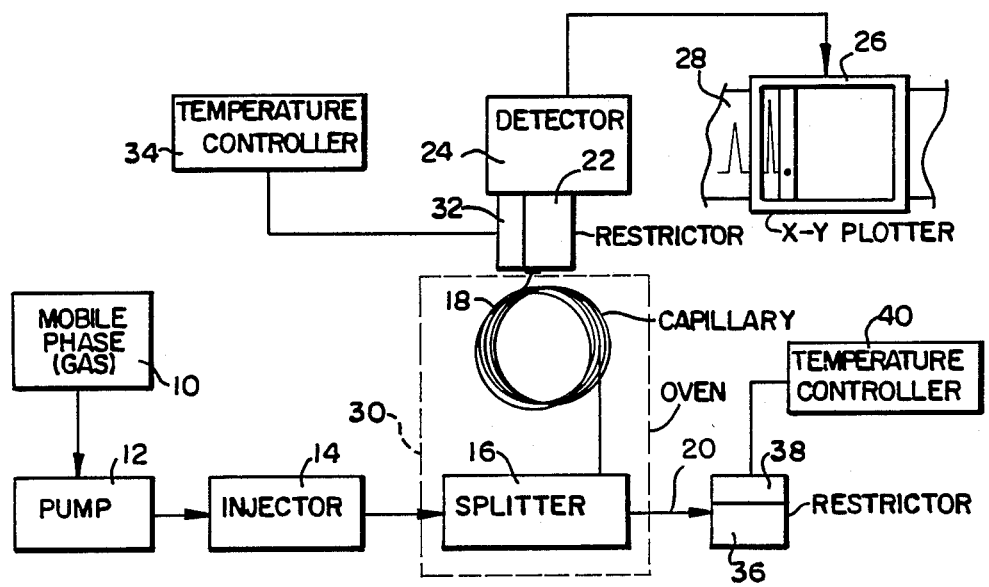
FIG. 4 is a block diagram of an SFC system incorporating the present invention.

As shown in FIG. 4, a mobile phase fluid is supplied from a source 10 to pump 12. The mobile phase is provided by pump 12 under pressure through injector 14 to splitter 16. A sample (not shown) to be analyzed is injected into the mobile phase stream by injector 14. Pump 12, injector 14, splitter 16 and the means for interconnection are all known. For purposes of the present description, it is preferred that pump 12 be programmable so that mobile phase pressure can be fixed to preselected values and modified to increase pressure at various rates during a test run.

Splitter 16 provides a portion of the mobile phase/sample combination to capillary 18 and the remaining to a non-analyzed output 20. The ratio between that portion provided to capillary 18 and that provided to output 20 is known as the split ratio. As is known, the split ratio is the ratio of flow into the capillary to flow into the non-analyzed output.

In the preferred embodiment, capillary 18 is 10 meters long and has an internal diameter of 50 microns. Since capillary SFC requires the mobile phase to be subjected to predetermined pressure conditions while in the capillary, it is known and preferred that the pressure in capillary 18 be controlled by pump 12.

Since pressure conditions are to be maintained in capillary 18, a restrictor 22 is attached in any known manner to the outlet end of capillary 18. In the preferred embodiment restrictor 22 is a fused silica restrictor having an internal diameter of less than 10 microns, a length of 1 centimeter and an outside diameter of about 300 microns. Restrictor 22 is also fixed in the base of detector 24. While detector 24 can be any known detector, for the purposes of the present description it is preferred that detector 24 be a gas chromatography Flame Ionization detector. The output of detector 24 in the preferred embodiment, is a voltage signal which is applied to the input of plotter 26. Plotter 26 creates a chart 28 over time of the detector output voltage. Such charts are known as chromatographs.

Since in SFC the mobile phase must be heated to a temperature above its critical temperature, splitter 16, capillary 18 and restrictor 22 are placed within a temperature controlled oven 30. Although the mobile phase fluid need be supercritical only in the column, i.e. only the capillary need be placed in the oven, I have chosen to place the splitter in the oven as well. For purposes of the present invention any commercially available oven can be utilized which is capable of maintaining the temperature of the mobile phase above its critical temperature.

Figure 3:
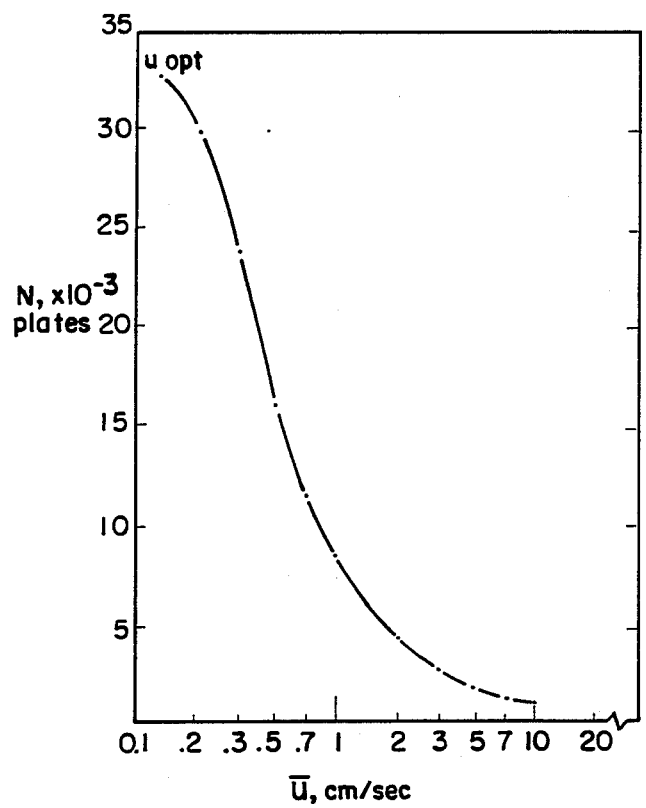
FIG. 3 is a graph of Efficiency (theoretical plates N) vs. Linear Velocity (u) which shows that as linear velocity increases, efficiency decreases.

As indicated previously in relation to FIG. 3, efficiency decreases as linear velocity increases. I have found that linear velocity of the mobile phase in capillary 18 can be controlled during programmed pressure operation utilizing the density and viscosity properties of the mobile phase within restrictor 22 by adjusting the temperature of the fluid within restrictor 22. Apparatus for controlling linear velocity is shown in FIG. 4 to include heater 32 mounted in heat transfer relationship with restrictor 22 for heating fluid within restrictor 22. The temperature maintained by heater 32 is regulated by temperature controller 34.

Since pressure is to be maintained in splitter 16 during operation, a second restrictor 36 is placed on the non-analyzed output 20. The linear velocity of fluid passing through restrictor 36 is controlled by a second heater 38 mounted in heat transfer relationship with restrictor 36. The temperature maintained by heater 38 is regulated by temperature controller 40. Since gas chromatographic detectors will be utilized in conjunction with the present invention, there may be a desire to use the heater zone found in the base of certain detectors to program restrictor temperature. However, simply using an existing heated zone to controllably change temperature is not adequate. The zone must be short enough to not prematurely raise the temperature of the mobile fluid. If this happens mobile phase density can drop precipitously along with solute solubility. Solutes tend to be lost inside the restrictor giving erroneous results in downstream detectors or even plugging the restrictor. To prevent this phenomena the heated zone must be as short as possible and relatively well matched to the length of the restrictor, i.e. the length where most of the internal pressure drop occurs. In addition the heated zone internal diameter surrounding the restrictor must be as small as possible to allow close contact between restrictor and heated zone. For rapid changes in temperature the zone thermal mass should also be as small as possible which will also serve to limit power requirements.

The shortness of the heated zone and maximum restrictor ID allowable is determined by constraints in heat transfer through the restrictor and into the fluid. If the restrictor is very short it will necessarily have a very small ID. Fluid might be in contact with it for only very short times. Even at column linear velocity of 10 cm/sec, contact time in a 1 cm long column length is 1/10th sec. if the restrictor diameter is 1/10th column diameter, its volume and contact time are 1/100th sec. Since velocity will increase with expansion as much as 500 times across the restrictor, contact time could drop to tens of microseconds or less.

Rough measurements of power requirements to heat supercritical $CO_2$ show on average about $2.5 \times 10^{-3}$ watt-sec/g-degree K is needed to raise fluid temperature in the restrictor of the preferred embodiment. If worst case mass flow is about $200 \times 10^{-6}$ g/sec and the largest difference between column and restrictor temperature is 760 degrees, then a worst case heat transfer requirement is approximately 2 milliwatts per degree rise or about 1.5 watts continuous power to raise temperature from 40 to 800 degree C. Transferring even this low power level through the walls of a very small restrictor is difficult. Increasing restrictor length increases contact time but also increases the probability of solutes dropping out of solution in the restrictor.

A heat transfer calculation indicates that a 300 um OD, 10 UM ID, 1 cm long restrictor, with a heat transfer coefficient of 1 watt/degree K-meter would allow passage of the maximum required power into the fluid. This assumes intimate contact of the heater with the exterior surface of the restrictor. If intimate contact does not exist, additional power will be required. Decreasing restrictor wall thickness or increasing length make adequate heat transfer more likely. The expansion will become more nearly isothermal than adibatic, somewhat perturbing mass flow rate calculations, but this effect is not large.

Under certain temperature conditions, thermal decomposition may occur but since the chromatography has already been carried out before the solute reaches the restrictor the main concern should be whether thermal breakdown products are lost in the restrictor. If they can be transported to the detector without serious loss of mass an appropriate response can probably still be obtained. Of course some structural information on labile molecules would be lost.

Very long restrictors drop virtually all of the system pressure inside the restrictor. This means fluid density inside the restrictor becomes very low, solutes tend to drop out of solution and stick to the walls or form particles which also can cause detector spiking. Long restrictors also tend to operate more isothermally than short adiabatic expansion devices. This will tend to further decrease density and viscosity at any point along the restrictor. Solute solubility will decrease, linear velocity will increase and so will solute volatility. Detector spiking due to solvent particles will likely decrease, but spiking due to solute particles may increase. Enhanced volatility and linear velocity should tend to deliver more of the solutes to the detector instead of the restrictor walls. This all suggests that such restrictors should be avoided whenever possible. The shortest, smallest ID restrictor yielding appropriate mass flow rates should always be used. This further means the heated zone length should match restrictor length or be no more than some small multiple of restrictor length, i.e. less then five times.

Consider now the structure shown in FIG. 5. Fixed in the wall insulation 50 of oven 30 is thermal block 52. Thermal block 52 is shown to have a centrally located bore 54 into which a thermally conductive adapter 56 has been located. Adapter 56 is positioned in intimate contact along a portion of its length with block 52 such that a heat transfer relationship is obtained. Adapter 56 is provided with a centrally located bore 58 having a narrow diameter on the order of 400 microns. Capillary 18 having a restrictor 22 attached to its outlet end is held within bore 58 by a press fit seal (not shown) or other suitable means. Heat is applied to block 52 by means of voltage controlled cartridge heater 60 inserted in a suitable bore. In order to assure that the temperature of block 52 is at a desired level a sensor 62 (for example a thermistor) is inserted in a further bore 64. The voltage signal used to control heater 60 is generated by temperature controller 34. Although not shown in detail, the circuitry of temperature controller 34 can be of any known design capable of receiving the signal from sensor 62 and regulating the output of heater 60 such that heat is applied to the restrictor fluid according to the temperature requirements described hereinafter.

Since the particular detector shown in FIG. 5 is a gas chromatograph flame ionization detector, a further series of bores is provided for the introduction of hydrogen (bore 66 in block 52 and bore 68 in adapter 56) and oxygen (bore 70). It will be noted that the structure of FIG. 5 calls for the passage of hydrogen through bore 68. Consequently, it should be kept in mind that the power requirements to heat the restrictor fluid may have to be increased to account for any heat transfer loss.

Consider now how the use of the previously described apparatus controls the linear velocity of fluid in a capillary SFC. Again, control of the linear velocity of fluid in capillary SFC is achieved by restrictor temperature programming to affect mobile phase viscosity and density changes.

It is desirable to start initially with a low restrictor temperature and increase this temperature with increasing column pressure. This approach is best accomplished utilizing a restrictor material with a small tempco such as fused silica since increasing ID with increasing temperature partially negates the desired effect. Changes in restrictor diameter are generally related to the operating temperature range divided by the material melting point. Therefore, it is desirable to use restrictor material with very high melting points such as fused silica or platinum to minimize diameter changes.

For the most useful capillary SFC conditions, fluid flow through the restrictor is laminar. Restrictors exhibiting this laminar fluid flow will exhibit worst case increases in linear velocity vs. pressure. The Poiseuille equation will apply if average viscosity is used.

Poiseuille Eq.

$$P = \frac{8L(R)\, \eta(R)\, V(R)}{\pi\, (r(R))^4\, K} \qquad (1)$$

Where P is system head pressure in Atmospheres, L(R) is restrictor length, $\eta(R)$ is the average fluid viscosity in the restrictor, r(r) is restrictor radius, K is a conversion constant and V(R) is volumetric flow rate.

Since volumetric flow equals mass flow divided by density the Poiseuille equation can be rewritten in terms of mass flow and average density as follows:

$$P = \frac{8L(R)\, F(R)}{\pi\, (r(R))^4\, K} \times \frac{\eta(R)}{\rho(R)} \qquad (2)$$

Where F(R) is the mass flow in the restrictor and $\rho(R)$ is the average density in the restrictor.

Implicit in this equation is the relationship between pressure and length down the restrictor. Knowing the relationship between pressure and density at any temperature allows us to accurately estimate average density in the restrictor.

To determine mobile phase linear velocity in the column we must know column mass flow and density. Since under steady state conditions mass flow past any one point must equal the mass flow past any other point, column mass flow must equal restrictor mass flow. If we assume pressure drop across the column is negligible, the whole column will have the same density. Knowing column head pressure and temperature the column density ($\rho(C)$) can be found in Gas Encyclopedia, English translation by Nissin Marshall, Elsevier Scientific Publishing Co., U.S. Distributor - Elsevier/North-Holland, Inc. New York, N.Y., 1976 (hereafter Gas Encyclopedia).

It was shown that:

$$\bar{u} = \frac{F(C)}{\rho(C)A} \quad (3)$$

Where $\bar{u}$ is column average linear velocity and A is column cross sectional area. Since:

$$F(C) = F(R) \quad (4)$$

for a steady state condition, utilizing the previous equations for volumetric flow and pressure one can arrive at the following equation for linear velocity.

$$\bar{u} = \frac{(r(R))^4 K}{\pi 8 L(R)} \times \frac{P}{A} \times \frac{\rho(R)}{\eta(R)} \times \frac{1}{\rho(C)} \quad (5)$$

Simplifying and combining constants yields:

$$\bar{u} = K' \frac{\rho(R)}{\eta(R)} \frac{P}{\rho(C)} \quad (6)$$

Column and restrictor dimension are included in the constant K'. Changing restrictor temperature to produce an effect where $(\rho(R)/\eta(R))$ is inversely proportional to $(P/\rho(C))$, results in column linear velocity remaining constant with increasing pressure. Since density, and to a lesser extent, viscosity change with pressure the simplest approach to finding such conditions is graphical. Changes in $(\rho(R)/\eta(R))(P/\rho(C))$ were calculated for a $CO_2$ mobile phase above its critical temperature and plotted vs. P for a number of column and restrictor temperatures. In calculating these various linear velocity values it was helpful to use the viscosity and density levels shown in Gas Encyclopedia.

To calculate desired linear velocity using (6), one could calculate column density, $\rho(C)$, since pressure and capillary temperature are known. Likewise, restrictor density, $\rho(R)$, can be calculated. However, viscosity is less accurately calculable since it is a function of both pressure and temperature in a non-ideal way. A more tractable approach is to prepare tables of the ratio $\rho(R)/\eta(R)$ versus pressure (P) at multiple temperatures. For temperatures between the table values, extrapolation is required. If a computer is utilized, as in the preferred embodiment (not shown in the drawings), the data in the prepared tables can be extrapolated by subjecting the data to any known form of non-linear "best fit" mathematical reduction. Simple linear extrapolation will suffice unless the data is known to be very non-linear in the region of extrapolation.

Figure 7:
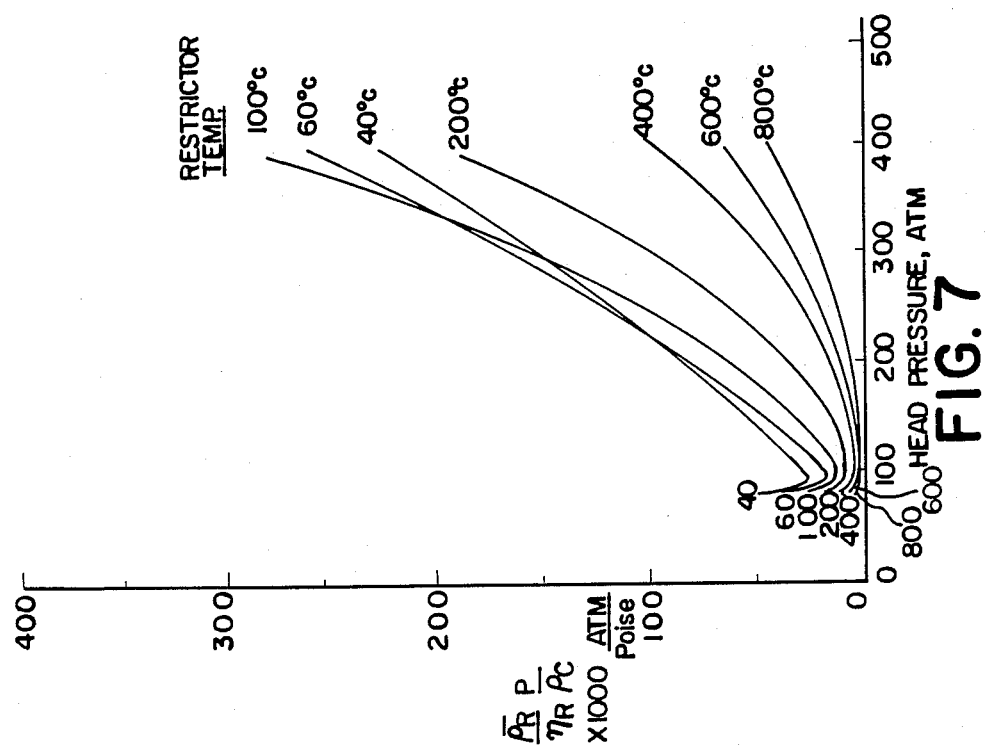
FIG. 7 is a graph of calculated linear velocity vs. pressure where the chromatographic column is heated to 200° C. and the restrictor is heated to various temperatures from 40° C. to 800° C.

The results of the calculations for a $CO_2$ mobile phase are presented in FIGS. 6 and 7 with each figure consolidating the results at a single column temperature. The range of column temperatures between 40 and 200 degrees C covers most of the useful density range of capillary SFC with $CO_2$ as the mobile phase. The actual values of linear velocity depend on K' which combines restrictor and column dimensions.

In order to determine the appropriate restrictor temperature to maintain constant column linear velocity during pressure change, I have solved for temperature utilizing the following:

$$\rho(C)/P = K' (\rho(R)/\eta(R)) \quad (7)$$

However, determining the initial temperature which will yield a desired linear velocity requires solving (6) for temperature at a desired linear velocity at a particular pressure. It should be kept in mind that $\rho(R)$ and $\eta(R)$ are not independently variable.

Figure 8:
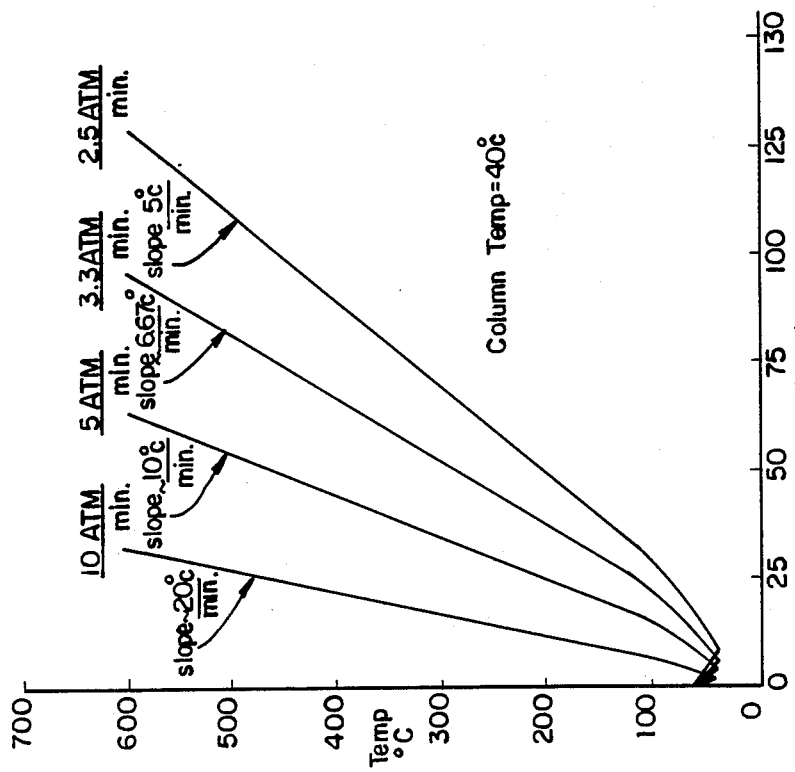
FIG. 8 is a graph of calculated temperatures over time for maintaining linear velocity constant in a chromatograph as pressure is increased at various rates from 2.5 ATM/min. to 10 ATM/min.

The temperature vs. time profiles necessary to maintain constant column linear velocity during various linear pressure ramps are shown in FIG. 8. This data was obtained by finding those restrictor temperatures from tables (not shown), generated with respect to FIGS. 6 and 7, and solving (7). This was done by finding the temperature at which a particular $\rho(R)/\eta(R)$ exactly offset changes in $P/\rho(C)$ during pressure programming. These curves represent temperature programming necessary to maintain constant linear viscosity in a capillary SFC system similar to that shown in FIG. 4 wherein a pressure program from 80 to 400 ATM at ramp rates from 2.5 to 10 ATM/min. are used with a $CO_2$ mobile phase at 40 degrees C in the capillary. After some relatively small nonlinear perturbations near 80 ATM, where density changes very rapidly with pressure, the temperature vs. time profiles become quite linear with slopes of 5-20 degrees C/min. These temperatures do not vary rapidly or have an unrealistically narrow temperature control band.

Figure 1:
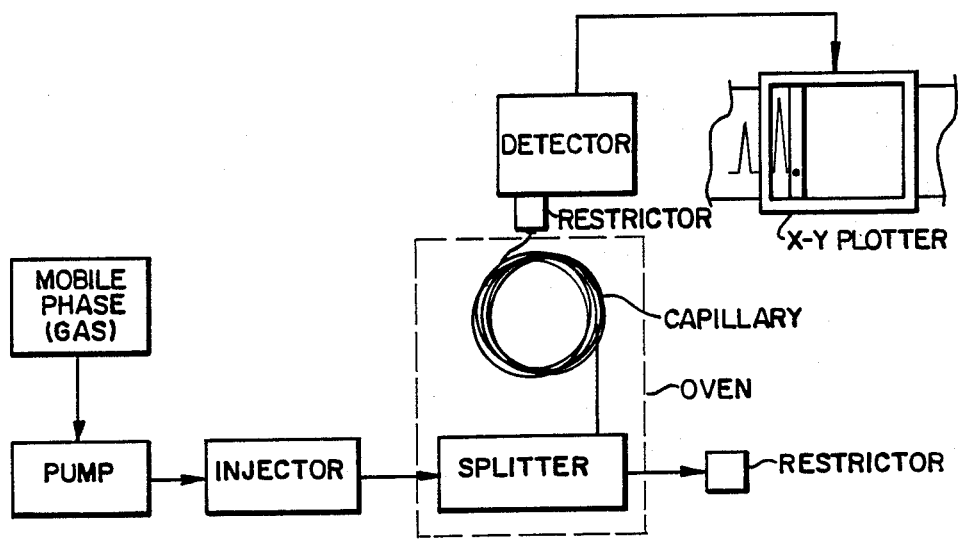
FIG. 1 is a block diagram of a prior art supercritical fluid chromatography system.
Figure 2:
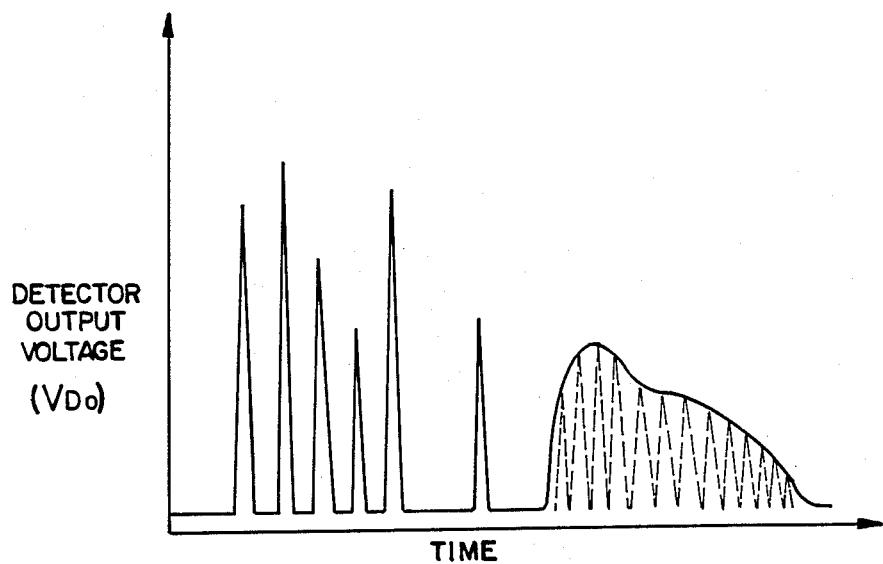
FIG. 2 is an example of an SFC chromatogram wherein resolution has degraded towards the end of the test run.

Temperature can be programmed to yield different column linear velocities in different parts of the run in order to customize an analysis for the optimum speed/resolution trade off. For example, in those test run portions where resolution is more than adequate, linear velocity can be increased. Conversely, in those test run portions where resolution is poor, for example FIG. 2, linear velocity can be held constant or even decreased. Thus, by controlling linear velocity resolution can be maximized and test duration can be minimized.

It should also be understood that a beneficial result of the above is also achieved in the incorporation of linear velocity control on the non-analyzed output 20 of splitter 16. By controlling the linear velocity of output 20 the split ratio can be more precisely controlled. As will be appreciated after reading the above, controlling the linear velocity results in a controlled mass flow. The ratio of mass flow in the capillary to non-analyzed splitter output is the split ratio. In prior devices changing operating conditions also varies the split ratio, requiring a recalculation with each operating change. Utilizing the linear velocity control disclosed herein, the split ratio can be maintained constant by making compensating adjustments to the non-analyzed output as linear velocity in the column is changed.

For more turbulent flow restrictors, utilizing the present invention to decrease column linear velocity yields a more pronounced effect and thus wider control bands.

Simple straight line restrictor temperature profiles can be generated using linear ramp generators in a temperature controller. For more complex shapes or high reproducibility, restrictor temperature control should be synchronized with column pressure. As the above indicates, any desired linear velocity vs. head pressure profile within the control limits can be accurately followed if restrictor geometry, column ID, and mobile fluid identity are known. This also requires a knowledge of density and viscosity of the mobile phase fluid vs. temperature and pressure. In the absence of an adjustable flow controller the present invention allows linear velocity to be accurately controlled.

While the invention has been described and illustrated with reference to specific embodiments, those skilled in the art will recognize that modifications and variations may be made without departing from the principles of the invention as described herein above and set forth in the following claims.

I claim:

1. A system for analyzing a sample by chromatographic separation of said sample into components, comprising: a stationary phase member, having inlet and outlet ends; mobile phase introduction means for introducing a mobile phase to said inlet end of said stationary phase member; injection means for injecting a sample into said mobile phase prior to introduction to said inlet end; pressure means for subjecting said mobile phase while passing through said stationary phase member to a preselected pressure; temperature means for subjecting said mobile phase while passing through said stationary phase member to a preselected temperature; a restrictor attached to said outlet end of said stationary phase member; detection means for detecting said components; and linear velocity control means for controlling the linear velocity of said mobile phase, said control means comprising heater means which transfers heat to said restrictor, for heating said mobile phase in said restrictor so that as said pressure means modifies the mobile phase pressure the linear velocity of said mobile phase is maintained at a desired level by modifying the temperature of said mobile phase in said restrictor.

2. The system of claim 1, wherein said heater means comprises a thermally conductive block mounted in heat transfer relationship with said restrictor, a heater mounted in heat transfer relationship with said block which heater is responsive to a control signal, a sensor mounted to sense the temperature of said block, and heater control means, connected to said sensor and said heater, for receiving the sensed temperature of said block and generating a control signal to said heater to adjust the temperature of said block to a desired level.

3. The system of claim 1, wherein the temperature of said mobile phase in said restrictor is modified to a calculated value, said calculated temperature value being determined from the equation:

$$\rho(C)/P = K'[\rho(R)/\eta(R)]$$

Where
$\rho(C)$ is the mobile phase column density;
P is the pressure;
K' is a constant;
$\rho(R)$ is the mobile phase density in the restrictor; and
$\eta(R)$ is the mobile phase viscosity in the restrictor.

4. The system of claim 1, wherein said mobile phase has a critical temperature and wherein said temperature means maintains the temperature of said mobile phase in said stationary phase means at or above said critical temperature.

5. The system of claim 1, wherein said pressure means is programmable for at least a portion of the time said system is analyzing said sample and wherein said linear velocity control means is also programmable for at least said same portion of time so that as the mobile phase pressure is changed said linear velocity control means changes the temperature of said mobile phase in said restrictor maintaining the linear velocity of said mobile phase in said stationary phase member at a desired level.

6. The system of claim 1, further comprising splitter means for splitting off a desired flow of said mobile phase, into which said sample has been injected, for presentation to said inlet end and for providing the remaining flow to an output; a second restrictor attached to said splitter means output; and a second linear velocity control means comprising a second heater means mounted in heat transfer relationship with said second restrictor, so that the mass flow of said mobile phase in said second restrictor can be maintained at a desired level.

7. An apparatus for controlling the linear velocity of a pressurized mobile phase in a chromatographic analysis system comprising: a restrictor through which the mobile phase passes, and heater means, which transfers heat to said restrictor, for heating said mobile phase in said restrictor so that for a given mobile phase pressure the linear velocity of said mobile phase in said stationary phase member is maintained at a preselected level by modifying the temperature of said mobile phase in said restrictor.

8. The apparatus of claim 7, wherein said heater means comprises a thermally conductive block mounted in heat transfer relationship with said restrictor, a heater mounted in heat transfer relationship with said block which heater is responsive to a control signal, a sensor mounted to sense the temperature of said block, and heater control means, connected to said sensor and said heater, for receiving the sensed temperature of said block and generating a control signal to said heater to adjust the temperature of said block to a desired level.

9. A method for analyzing a sample by chromatographic separation of said sample into components, comprising the steps of:
introducing a mobile phase to the inlet end of a stationary phase member;
heating said mobile phase in said stationary phase member to a preselected temperature;
injecting said sample into said mobile phase;
pressurizing said mobile phase to a preselected pressure;
passing said mobile phase through a restrictor attached to the outlet end of said stationary phase member;
maintaining the linear velocity of said mobile phase in said stationary phase member at a preselected level by heating said mobile phase as it passes through said restrictor; and
detecting said components.

10. The method of claim 9, further comprising the steps of determining the linear velocity characteristics of the mobile phase with regard to the structure of the stationary phase member as the mobile phase pressure is increased; determining the mobile phase temperature required to maintain the linear velocity at a desired level for a given mobile phase pressure; and heating said mobile phase in said restrictor to said determined mobile phase temperature.

11. A method for controlling the linear velocity of a pressurized mobile phase in a chromatographic analysis system comprising the steps of: passing said mobile phase through a restrictor, and heating said mobile phase in said restrictor so that for a given mobile phase pressure the linear velocity of said mobile phase in said stationary phase member is maintained at a preselected level by modifying the temperature of said mobile phase in said restrictor.

12. The method of claim 11, wherein said mobile phase is maintained at a first temperature in said stationary phase member, further comprising the steps of: determining the ratio of pressure over density $[P/\rho(C)]$ at said first temperature and at various pressures for said mobile phase in said stationary phase member, determining the ratio of $\rho(R)/\eta(R)$ of said mobile phase at said various pressures and at different temperatures, selecting a second temperature from said different temperatures, said second temperature being the temperature to which said mobile phase is heated in said restrictor, said second temperature being selected so that for any one of said various pressures the following equation is maintained:

$$\rho(C)/P = K'[\rho(R)/\eta(R)].$$

* * * * *